(12) United States Patent
Konry et al.

(10) Patent No.: US 12,064,768 B2
(45) Date of Patent: Aug. 20, 2024

(54) SINGLE CELL ISOLATION AND PROCESSING SYSTEM WITH REVERSIBLE WELL SHAPE

(71) Applicant: Northeastern University, Boston, MA (US)

(72) Inventors: Tania Konry, Boston, MA (US); Giovanni Ugolini, Allston, MA (US)

(73) Assignee: Northeastern University, Boston, MA (US)

( * ) Notice: Subject to any disclaimer, the term of this patent is extended or adjusted under 35 U.S.C. 154(b) by 551 days.

(21) Appl. No.: 17/182,160

(22) Filed: Feb. 22, 2021

(65) Prior Publication Data

US 2021/0260576 A1    Aug. 26, 2021

Related U.S. Application Data

(60) Provisional application No. 62/980,128, filed on Feb. 21, 2020.

(51) Int. Cl.
*B01L 3/00* (2006.01)

(52) U.S. Cl.
CPC ..... *B01L 3/5085* (2013.01); *B01L 2300/0829* (2013.01); *B01L 2400/049* (2013.01)

(58) Field of Classification Search
CPC .............................. B01L 3/5085; C12M 47/04
See application file for complete search history.

(56) References Cited

U.S. PATENT DOCUMENTS

| | | | |
|---|---|---|---|
| 2013/0115686 A1* | 5/2013 | Park | B01L 3/502 |
| | | | 137/15.01 |
| 2016/0288120 A1* | 10/2016 | Song | B01L 3/50853 |

FOREIGN PATENT DOCUMENTS

| | | |
|---|---|---|
| WO | 2010085275 A1 | 7/2010 |
| WO | 2014031997 A1 | 2/2014 |

* cited by examiner

*Primary Examiner* — Natalia Levkovich
(74) *Attorney, Agent, or Firm* — Verrill Dana, LLP

(57) ABSTRACT

The technology provides arrays of microwells with reversible shape for culture, analysis, and recovery of individual cells or groups of cells. The microwells are reversibly formed by vacuum-induced deflection of an elastomeric membrane into an array of microwell molds formed in a microwell substrate. The shape of each microwell or groups of microwells can be selectively altered by applying or releasing vacuum to individual microwells. The devices, systems, and methods utilizing the technology enable collection of individual cells for further study or therapeutic use without the need for micromanipulation.

10 Claims, 3 Drawing Sheets

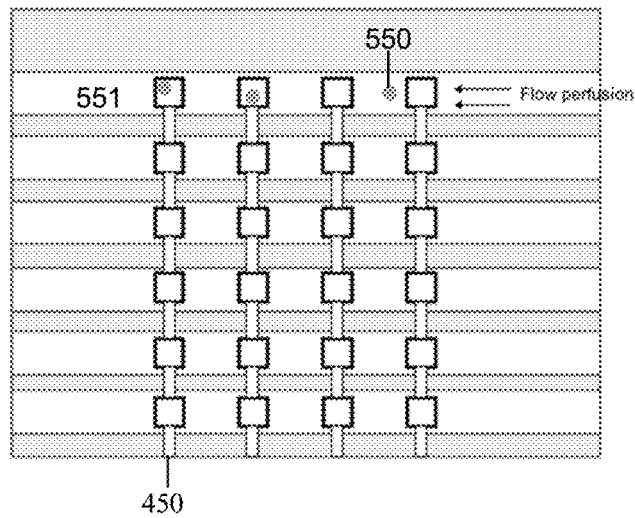
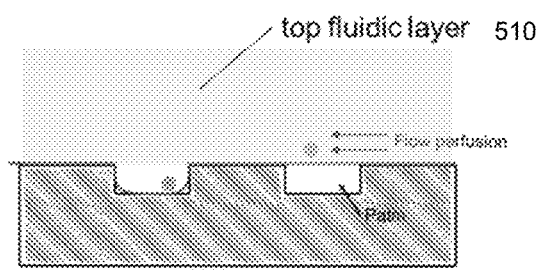
FIG. 5A  FIG. 5B
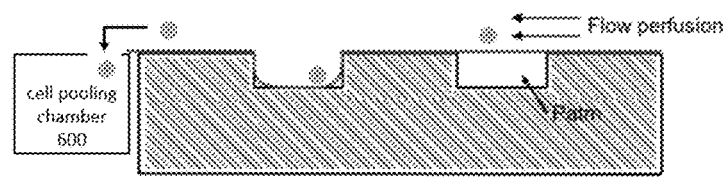
FIG. 6

SINGLE CELL ISOLATION AND PROCESSING SYSTEM WITH REVERSIBLE WELL SHAPE

CROSS-REFERENCE TO RELATED APPLICATIONS

This application claims priority to U.S. Provisional Application No. 62/980,128, filed 21 Feb. 2020, which is incorporated by reference herein in its entirety.

BACKGROUND

Arrays of microwells are useful to screen, separate, or analyze cell populations and to culture or image them. The microwells of microfluidic devices are typically monolithic and permanently formed into a solid material. Cells of interest can be recovered via micromanipulation techniques, but these are operationally complex, expensive, time-consuming, low-throughput, and difficult to automate. Planning recovery of desired cells can significantly add to the cost, complexity, and design of screening experiments. While cells can be screened for desired phenotypes using microwell arrays, and experiments can be designed to expose cells to conditions to reveal desired cell types, subsequently isolating and cultivating the most desirable cells from typical microwells involves significant complications and delays experimental progress. Single cell analyses are of increasing interest and can overcome the heterogeneity of cellular processes involving groups of individual cells, such as cellular interactions and secretion of cellular products. Thus, there is a need to provide facile and uncomplicated techniques for isolation and cultivation of desirable individual cells, particularly following their cultivation in microwells.

SUMMARY

The present technology provides microwells for culture, isolation, and analysis of individual cells or groups of cells, wherein the microwells have variable shape to aid in cell manipulation and recovery. Changes in microwell shape are induced by vacuum applied beneath a thin deformable membrane disposed over an opening in a microwell form or mold in a solid substrate, through the use of pneumatic channels embedded in the substrate. For example, the shape of each microwell can be selectively and reversibly altered by applying and releasing vacuum to the space between a thin elastic membrane that covers the opening of a microwell mold. The membrane can cover an entire array of microwell molds in a microwell substrate. When the elastomeric membrane is drawn down into the mold, it forms a microwell. The form of individual microwells or groups of microwells can be controlled via a controlled vacuum source. When the vacuum is reduced, returning partially or entirely back to atmospheric pressure, the elastomeric membrane relaxes back towards its original position, forming a planar surface at the opening in the microwell substrate and elevating a desired cell or group of cells into position above the microwell mold and microwell substrate, from where it can be released, captured, and transferred, by simple application of flow or by micromanipulation, to another location for further study or use. The cell recover process optionally can be automated.

Unselected cells, whose microwells remain under vacuum while harvesting cells of interest, remain trapped in their microwells, allowing the raised, selected cells of interest to be directed towards an outlet. The release of vacuum from beneath the thin membrane of selected cells can be automated and computer controlled, or can be manually controlled. For example, the technology provides cell recovery after assay and can allow correlation of phenotype or genotype features with the assay results (either secretomic or functional assay) at the single cell level. The technology can be utilized for single cell analyses for immunotherapy, single cell proteomics, and rapid screening. The single cell manipulation system of the present technology can be applied, for example, to analysis of tumor cell interactions with subsequent on-demand release of cells having known identified functional activity. The system also can be applied to screening of secreted biomolecules at the single cell level with subsequent on-demand collection and release of cells with known secretion products or secretion levels.

The present technology can be further summarized by the following list of features.

1. A microwell device for isolating, processing, or analyzing cells, the device comprising: a microwell substrate comprising a plurality of microwell molds, each microwell mold having an opening at an upper surface of the substrate, and one or more pneumatic microchannels connecting the microwells to an inlet for attaching a controllable vacuum source; and an elastomeric membrane bonded to the upper surface of the substrate and covering said microwell mold openings; wherein the elastomeric membrane is capable of conforming to each microwell mold when vacuum from said controllable vacuum source is applied through a said pneumatic microchannel connected to said microwell mold, thereby forming a microwell, and is capable of relaxing to form a planar surface above each microwell mold when pressure in the pneumatic microchannel connected to said microwell mold is returned to atmospheric pressure.

2. The microwell device of feature 1, wherein the microwell molds are arranged as a rectangular array having rows and columns of microwell molds, and wherein a unique pneumatic microchannel connects the microwell molds of each row or a unique pneumatic microchannel connects the microwell molds of each column of the array.

3. The microwell device of feature 1 or 2, further comprising one or more perfusion channels configured for washing cells from the planar surface of the elastomeric membrane above each microwell mold when pressure in the microwell mold is at atmospheric pressure.

4. The microwell device of feature 3, wherein the one or more perfusion channels comprise a plurality of perfusion channels configured for washing cells from the planar surface of the elastomeric membrane above each microwell mold when pressure in the microwell mold is at atmospheric pressure, wherein a unique perfusion microchannel is disposed above the microwell molds of each row or a unique pneumatic microchannel connects the microwell molds of each column of the array, and wherein the perfusion microchannels of the device are orthogonal to the pneumatic microchannels of the device.

5. The microwell device of feature 3 or 4, further comprising a cell pooling chamber.

6. The microwell device of any of the preceding features, wherein the elastomeric membrane comprises polydimethylsiloxane, silicone rubber, acrylic elastomer, polyurethane, or a combination thereof.

7. The microwell device of any of the preceding features, wherein the elastomeric membrane has a thickness in the range from about 1 µm to about 20 µm.

8. The microwell device of any of the preceding features, wherein the elastomeric membrane comprises one or more selected cell binding moieties disposed on a surface of the membrane corresponding to an inner surface of one or more of said microwells.

9. The microwell device of feature 8, wherein the cell binding moieties are selected from the group consisting of antibodies, aptamers, antigens, proteins, nucleic acids, polysaccharides, and cells.

10. The microwell device of any of the preceding features, wherein the one or more pneumatic microchannels are configured to supply vacuum from said controllable vacuum source separately to each individual microwell mold.

11. The microwell device of any of the preceding features, wherein each of the microwell molds have a length or a diameter in the range from about 5 μm to about 100 μm.

12. A single cell isolation, processing, or analysis system comprising the microwell device of any of the preceding features, a controllable vacuum source connectable to the pneumatic microchannels and operative to deform the elastomeric membrane of the device, and optionally a controller for programmed operation of the controllable vacuum source and/or to direct vacuum to one or more selected pneumatic channels.

13. The system of feature 12, wherein the microwell device further comprises one or more perfusion channels configured for washing cells from the planar surface of the elastomeric membrane above each microwell mold when pressure in the microwell mold is at atmospheric pressure, and the controller further is capable of regulating perfusion of fluid through the one or more perfusion channels.

14. The system of feature 12 or 13, further comprising a digital imaging microscope and imaging processing software.

15. The system of any of features 12-14, wherein analysis, isolation, and/or processing of desired cells can be semi-automated or fully automated.

16. A method for analysis, isolation, and/or processing of a plurality of single cells, the method comprising:
    (a) providing the system of any of features 12-15;
    (b) applying vacuum to one or more microwell molds of the device, whereby the elastomeric membrane forms microwells in said microwell molds;
    (c) depositing a cell suspension onto the membrane of the device, whereby one or more cells of the cell suspension become entrapped within one or more of the microwells;
    (d) analyzing one or more cells entrapped within the microwells, whereby a characteristic of the one or more cells is determined; and
    (e) isolating and/or processing cells having a characteristic of interest.

17. The method of feature 16, wherein the method is performed without the use of a micromanipulator.

18. The method of feature 16 or 17, wherein the characteristic of the one or more cells is selected from the group consisting of an ability to produce antibodies or another cell secretion product, a secreted amount of antibodies or another cell secretion product, an immune cell-tumor cell interaction, expression of a gene, a cell phenotype, and a cell genotype.

19. The method of any of features 16-18, wherein the isolating and/or processing includes reducing vacuum applied to one or more microwell molds of the device.

20. The method of any of features 16-19, further comprising:
    (c1) allowing for one or more cells to bind to a cell binding moiety disposed on an inner surface of one or more of the microwells.

21. The method of any of features 16-20, wherein the analyzing includes use of a microscope, a digital imaging microscope, a fluorescence microscope, imaging processing software, performing genomic analysis, performing proteomic analysis, or a combination thereof.

22. The method of any of features 16-21, wherein a single cell is deposited into one or more of the microwells.

23. The method of any of features 16-22, further comprising:
    (f) removal of one or more cells from the device for further analysis, cultivation, expansion, or use in a therapeutic method.

24. The method of any of features 16-23, wherein the method includes reducing vacuum to one or more microwell molds of the device, whereby the elastomeric membrane relaxes above said microwell molds, the method further comprises perfusing a liquid over the relaxed membrane, thereby washing one or more cells from the membrane.

25. The method of feature 24, wherein the one or more cells washed from the membrane are collected in a cell pooling chamber of the device.

As used herein, the term "about" refers to a range of within plus or minus 10%, 5%, 1%, or 0.5% of the stated value.

As used herein, "consisting essentially of" allows the inclusion of materials or steps that do not materially affect the basic and novel characteristics of the claim. Any recitation herein of the term "comprising", particularly in a description of components of a composition or in a description of elements of a device, can be exchanged with "consisting essentially of" or "consisting of".

BRIEF DESCRIPTION OF THE DRAWINGS

FIG. 5A shows a microwell array having perfusion flow channels, and FIG. 5B shows a cross-section of the device of FIG. 5A with a top fluidic layer to apply flow perfusion across the membrane surface.

FIG. 6 shows an example of a process of transporting a cell by perfusion from a relaxed microwell to a pooling chamber in fluidic communication with a perfusion microchannel.

DETAILED DESCRIPTION

A device of the present technology includes a microwell substrate and an elastomeric membrane mounted on an upper surface of the substrate. The microwell substrate includes a plurality of microwell molds disposed in the upper surface of the substrate. The substrate can be a microstructured layer of solid material. The microwell molds determine the shape and profile of the microwells that are formed by applying vacuum beneath the membrane. The dimensions of the individual microwells can range from about 5 μm to about 100 μm or more (i.e., just sufficient for one or a few eukaryotic cells), and any desired shape can be used, including circular, square, or rectangular, for example. The plurality of microwells sharing a common substrate or chip can be arranged into a two-dimensional array, i.e., a planar array having length and height, optionally forming a rectangular array having rows and columns, which can be ordered orthogonally to each other. A microfluidic channel, group of channels, or circuit of channels can connect individual molds (preferably only one channel opening into each microwell mold, or two channels opening into each mold in the case where a row or column of molds is linked together and share a common level of vacuum.

The elastomeric membrane is thin, flexible, and deformable under negative pressure compared to atmospheric pressure. The membrane can have a thickness ranging from about 1 µm to about 50 µm, for example, or from about 1 µm to about 20 µm. The membrane can be bonded to the upper surface of the microwell substrate except at the openings of the microwell molds. The membrane can include or consist of a material such as polydimethylsiloxane (PDMS), a silicone rubber, or another elastomer that is non-toxic to cells under study. The elastomeric membrane can be bonded to the substrate by plasma treatment or another method.

Figure 1:
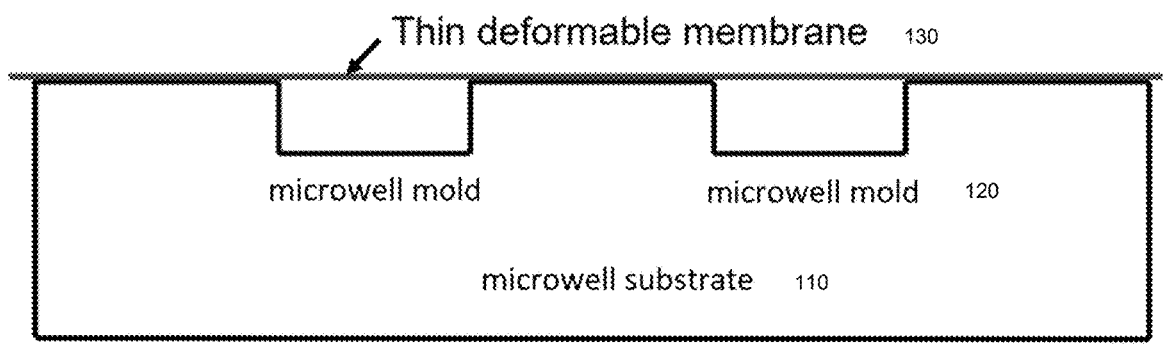
FIG. 1 depicts a cross section of a portion of a reversible microwell array device including a thin deformable membrane covering the openings of the microwell molds of the substrate.

FIG. 1 shows an example of thin deformable membrane 130 on the upper surface of microwell substrate 110. An array of microwell molds 120 are formed as indentations at an upper surface of the substrate.

Cell attachment to the membrane is optional. Many polymers (e.g., polyurethane) have surfaces that are not conducive to cell attachment, and as the majority of mammalian cells are attachment dependent, the culture surface can require modification. Modifying surface hydrophilicity, chemistry and roughness, and incubating biomaterials with extracellular matrix proteins, such as fibronectin, can have an enhancing effect on cell attachment. Surface modification of biomaterials has been accomplished using methods such gamma irradiation, ultraviolet irradiation, and plasma etching. Plasma etching, for example, can be utilized for membrane optimization as it is an effective method to induce stable changes to surface properties without significantly affecting the bulk material.

Figure 2:
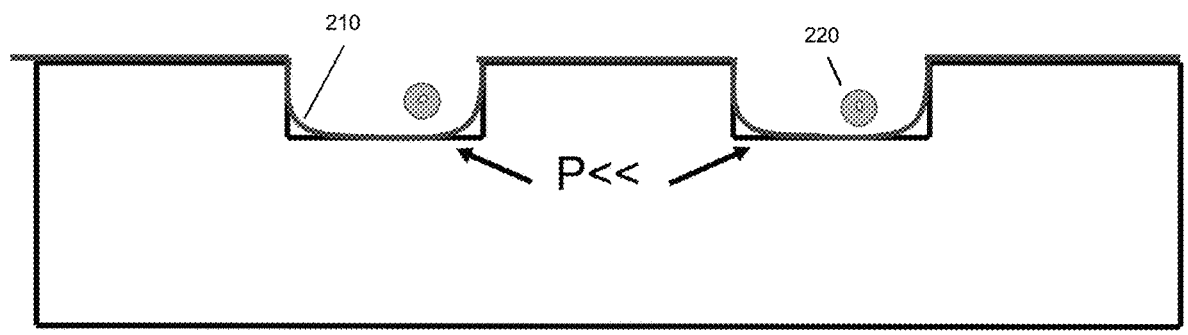
FIG. 2 shows the device of claim 1 after application of vacuum beneath the membrane at the microwell molds to form microwells. Single cells have been captured within the microwells.

The elastomeric, deformable membrane is capable of reversibly conforming to a microwell mold when vacuum is applied through a pneumatic microchannel to the microwell mold, thereby forming microwells 210 in the elastomeric membrane (see FIG. 2). To form a microwell, vacuum (negative pressure, shown as P<< in FIG. 2) can be applied to microchannel or pneumatic channel 450 (FIG. 4) embedded in the microwell substrate. The negative pressure applied to the microfluidic channel equilibrates with the pressure in the microwell molds. The deformable membrane then deflects into the microwell molds creating microwells 210 from the membrane where it conforms to the microwell molds.

A suspension of single cells or groups of cells can be placed on top of the membrane, and single cells or groups of cells can be allowed to settle onto the membrane under the influence of gravity, whereby single cells or groups of cells enter into the microwells. FIG. 2 shows a cross-section of the deformable membrane deflected into the well molds and forming microwells under vacuum, with cells 220 settled into the microwells. P<< indicates pressure lower than atmospheric pressure (atm) in the space between the deformable membrane and the microwell substrate.

Figure 3:
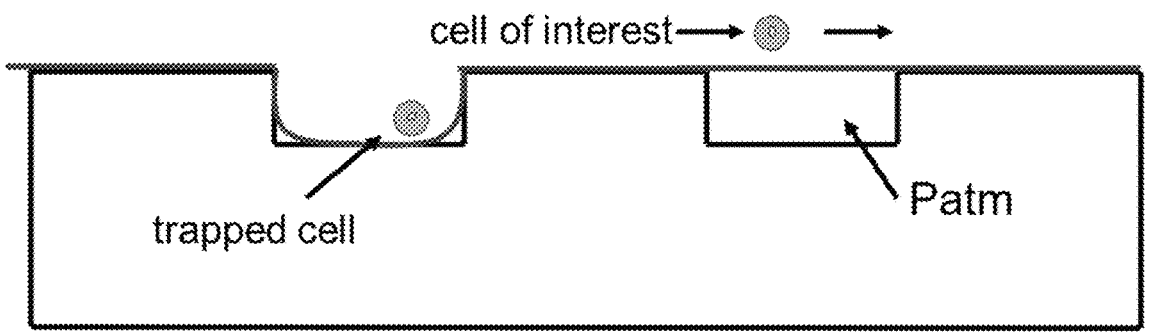
FIG. 3 illustrates a single cell of interest released from a relaxed microwell.

The elastomeric membrane is capable of relaxing to re-form a planar surface above a microwell mold when atmospheric pressure is applied (i.e., vacuum is released) to the microwell mold. FIG. 3 shows a side view of a single cell trapped in a microwell cavity (left), while a cell of interest has been released from a well (right) having relaxed configuration by release of vacuum at the specific microwell of interest. The pressure under the deformable membrane at the site of interest is indicated as about atmospheric pressure (Patm). After the desired culture time, experiment, or assay has elapsed, the vacuum can be released at specific sites of interest in order to lift the desired cells and expose them to the surface. The cell of interest can then be recovered/ isolated by application of flow or by mechanical means, such as with the use of a micromanipulator. The membrane upper surface can be washed with a physiological buffer solution or cell culture medium, leaving only the cells trapped in the cavities where vacuum is still applied. Optionally, desired cells can be collected at cell pooling chamber 600 (see FIG. 6). Unselected cells remain trapped in wells, as is shown by the trapped cell in FIG. 3, because flow of perfusion solution across can create laminar flow above the microwells, with little or no mixing of the microwell contents with the perfusion solution.

Each reversible microwell can be controlled individually, or in groups such as rows or columns, through either manual or automatic control. Micro-valves can be utilized to control of each reversible microwell. Various vacuum systems and pumps (see, e.g., welchvacuum.com) can be configured for use in the technology, and the entire system can be automated with integration of other analysis devices, imaging, microprocessors, and software. A controllable vacuum source can include, for example, tubing, regulators, needle valves, ball valves, microelectronics, microchips, nanoelectronic devices; microvalves, channels, or restrictions. Channels (microscale or nanoscale) can be utilized with electrical circuits, reservoirs, ports, holes, valves, air-filled spaces, fluid-filled spaces, waste receptacles, pump mechanisms, vacuum lines or ports, electrical devices or connections, circuitry, sensors, nanoelements (i.e., nanoparticles and/or nanotubes), biomolecules (including peptides, proteins, nucleic acids, carbohydrates, antibodies, lipids, growth factors, cytokines, or metabolites), surface coatings, membranes, membranes with pores, viewing panels, attached tubing or lines, display devices, microprocessors, software, memory devices, buttons, user interfaces, and wireless transmitters and/or receivers. Controllable liquid flow(s) can be configured utilizing similar technologies.

After release of vacuum at specific sites of interest in order to lift the desired cells and expose them to the surface (FIG. 3), recovery of selected cells by micromanipulation is substantially easier due to the cells not being trapped in the microwells but floating or slightly attached above on the surface of the thin deformable membrane. The difficult insertion of micropipettes directly into microwells can be avoided, making the recovery of selected cells cheaper and more user friendly, and avoiding the need for complex and costly precision cell handling equipment. After releasing the cells of interest, desired flow patterns can be applied to the surface of the device or chip to direct selected cells towards an outlet. If desired, the microwell device can be tilted during release of the cells (or cell groups) of interest, without releasing the trapped wells.

A cell handling system combines the reversible microwell array device described above with an added detection module for detection of biomolecules attached to individual cells and/or biomolecules secreted by individual cells. The detection module can be in the form of a glass slide patterned with capture antibodies that specifically bind proteins of interest. It also can be in the form of fibers holding microbeads coated with such capture antibodies. Additional detection modules or layers can be added.

Figure 4:
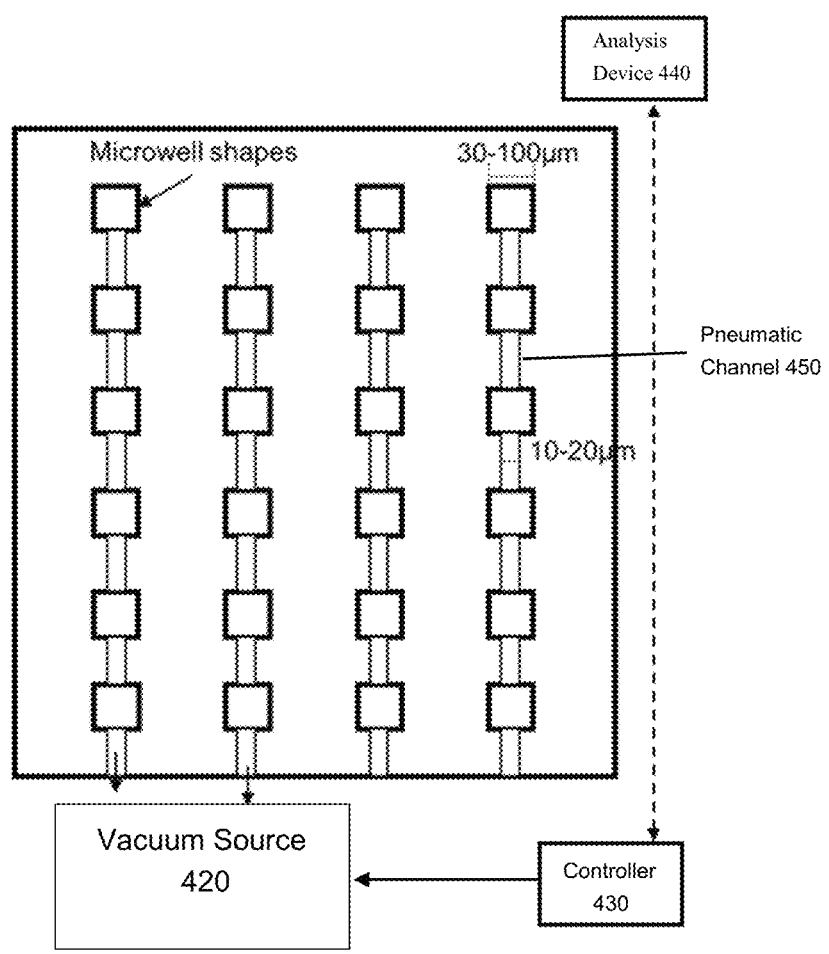
FIG. 4 shows a top view of a microwell device with pneumatic microchannels illustrated.

The microwell substrate can contain or consist of a polymer material or other non-toxic rigid material. The microwell molds can have any desired shape (for example, cubic or rounded) and size (for example, 5-100 μm or 30-100 μm on a side or a diameter) and can be fabricated through lithography and replica molding similar to standard microwells of microfluidic devices. However, unlike standard microwell arrays, the wells can be connected to a pneumatic circuit of one or more microchannels (for example, having diameter of about 10-20 μm) that lead to an inlet for connection to a vacuum and/or positive pressure source at a surface of the microwell substrate. FIG. 4 illustrates cubic microwell shapes from a top view perspective with pneumatic circuit microchannels connected to a pressure/vacuum source. A controller with optional analysis device can be utilized.

FIG. 4 shows a device in which each well is connected to a linear array or circuit of pneumatic microchannels. The pneumatic circuits 450 can be in any desired configuration; FIG. 4 shows one example of a suitable arrangement of pneumatic circuits. A controller can be utilized to actuate the circuits to isolate microwells of interest. The controller can optionally be in communication with a microscope or other analysis device 440 (FIG. 4). A single cell isolation, processing, or analysis system can include a microwell device with controller 430 for programmed application of vacuum to the pneumatic channels from controllable vacuum source 420. The analysis device can include a digital imaging microscope and imaging processing software. The device can be included in a high-throughput system and the device can be reusable with multiple cell screenings. For example, the device can be rinsed and reused.

In a manual operation mode, the user can connect the inlets for pressure/vacuum (FIG. 4) to a pressure/vacuum source by tubing. In order to form microwells, a vacuum of, for example, about 500 mm Hg can be applied; the appropriate vacuum will depend on the thickness and elasticity of the elastomeric membrane and configuration of the microwell molds. Greater vacuum levels can be utilized, but sufficiently applied vacuum can be observed when the elastomeric membrane conforms to the microwell molds. For example, the vacuum applied can be in the range from about 25 mm Hg (~3 kPa) to about 1000 mm Hg (~133 kPa), from about 75 mm Hg (~10 kPa) to about 600 mm Hg (~80 kPa), from about 75 mm Hg (~10 kPa) to about 500 mm Hg (~67 kPa), from about 100 mm Hg (~13 kPa) to about 500 mm Hg (~67 kPa), or from about 200 mm Hg (~27 kPa) to about 500 mm Hg (~67 kPa). The vacuum (volume) displacement required is small, and typically available laboratory vacuum source can be utilized; or various types of vacuum pumps can be utilized, for example, diaphragm pumps, micromembrane pumps, peristaltic pumps, or positive displacement pumps. The user then pipettes a cell suspension into the microwells. After a brief time (e.g., about 2 minutes) the cells can settle in the wells due to gravity. The user can then wash the top of the membrane with clean culture medium and optionally place the device into a Petri dish or other culture container with a sufficient amount of culture medium for culture or assay. After the culture or assay, the user can remove vacuum from or apply positive pressure to only wells of interest, or all wells, and the thin membrane will displace upwards, lifting the cells out of the microwell molds.

When a cell suspension is pipetted on top of the reversible microwell structures, single cells can occupy each well and thus become independent and separated from the others. Several tests can be run with standard microwells such as hybridoma cell profiling (to screen for only the single cells that produce antibodies), immune-tumor cell interaction (to screen for only the single cells that successfully kill tumors), or cellular secretion products. Such assays provide information on cell function at the single-cell level. To correlate this functional information with genomic information, or to make use of only a specific subset of cells, it may be important to selectively retrieve certain cells from the microwells. With the technology described herein, cells can be selectively recovered after such an assay from the microwells they occupied during the assay for further analyses (e.g., genomic/transcriptomic, expansion). In the past, harvesting of selected cells could be achieved with micromanipulators; however, this was costly, time consuming, and complex, since the user needs to insert a micropipette tip inside individual microwells to collect the desired cells.

The advantages of the present technology include cell sorting devices and methods that can be easily deployed in the lab, rapidly scaled up and automated if needed, while providing accurate and quick isolation of single cells of groups of cells. The technology can provide microwells having variable shapes induced by means other than, or in addition to, application of pneumatic means. Changes in microwell shape can be induced by, for example control signals such as electrical stimuli, electromagnetic radiation, temperature, pH, or shape memory elastomeric polymer effects.

The technology can provide high resolution isolation of cells (or groups of) within wells, utilizing various elastomeric membranes, which can be coated or derivatized with cell-selective moieties. Functional nanoparticles can be included in or bound to the elastomeric membranes, for example. The elastomeric membrane can include functionalization with partial or complete coatings and/or additional layers. For example, dextran, collagen, nucleic acids, oligonucleotide barcodes, antibodies, and aptamers can be covalently or non-covalently bound to the membrane to facilitate specific cell attachment.

The devices of the technology can include any element or feature commonly used in microfluidic or nanofluidic devices, in microelectronic or nanoelectronic devices, or in medical devices. For example these can include optionally in combinations, one or more channels (microscale or nanoscale), electrical circuits, reservoirs, ports, holes, valves, air-filled spaces, fluid-filled spaces, waste receptacles, pump mechanisms, vacuum lines or ports, electrical devices or connections, circuitry, sensors, nanoelements (i.e., nanoparticles and/or nanotubes), biomolecules (including peptides, proteins, nucleic acids, carbohydrates, antibodies, lipids, growth factors, cytokines, or metabolites), surface coatings of any kind, radioisotopes, membranes, membranes with pores, viewing panels, attached tubing or lines, display devices, microprocessors, software, memory devices, buttons, user interfaces, and wireless transmitters and/or receivers. The devices can be coupled with other devices operative to generate single cells, cell groups or suspensions of cells, viruses, biomolecules, microbes, or other analytes.

Suspensions including multicellular tumor groups, neurospheres, mammospheres, hepatospheres and embryoid bodies can be formed by flow perfusion/combination of suspensions of individual cell types along with polymer scaffolds of either collagen, alginate, matrigel, or a scaffold free flow solution. A vacuum can be applied to the microwells device depicted in FIG. 4, resulting in all microwells reversibly orienting to a trapping configuration (FIG. 2). Each suspension of cell groups can be diluted immediately after formation, by real-time flow dilution, for seeding into the microwells. The process can be automated for repeat generation/analyses. Through flow application of a suspension of each of the cell groups, individual groups are seeded on the array of FIG. 4. A separate array can be used for each different suspension of groups, although combinations of groups on a single array can also be used. Trapping of an individual cell group is depicted in FIG. 2 and can be confirmed by visual inspection. After cultivation of the groups (about 24 hrs), releasing the desired group(s) of interest (FIG. 3) from the microwells can be accomplished by releasing the vacuum to the microwell containing the group of interest and subsequently flowing the released group towards an edge of the microwells device. Real time visualization of the flow perfusion capture of a single group can be confirmed visually (FIG. 5A), depending on the cell group. Release of vacuum below the microwell containing the group of interest allows the deformable membrane to rise out of the microwell and displace the group in the microwell out of the well, exposing the raised group for easy recovery.

FIG. 5A and FIG. 5B show a microwell device having top fluidic layer 510, which can be used to apply a perfusion solution for the capture of cells 550 from relaxed microwells. The top fluidic layer can flow through perfusion channels 551, depicted in FIG. 5A as extending across horizontal rows of microwells, as one possible arrangement. With this feature, after a selected microwell is released and the selected cells are lifted up out of the microwell shape, the application of flow will move the selected cells towards an outlet while the other (unselected cells) will remain trapped in the remaining microwells. The top fluidic layer depicted in FIG. 5B can include an additional layer above the top fluidic layer (not shown), for example, as a containment, visualization, or binding layer. The perfusion flow optionally can direct desired cells to a cell pooling chamber 600 (see FIG. 6).

While FIG. 5A and FIG. 5B illustrate the concepts of a top perfusion layer, perfusion channels can be in a matrix or in a network of channels, allowing for single-cell isolation or pooling at desired locations on the chip or substrate, or at various distant collection locations. The perfusion channels can be in any desired configuration. The cell pooling chamber 600 depicted in FIG. 6 can include a plurality of cell pooling chambers, each in fluid communication with a perfusion channel from a combination of channels. For example, the perfusion channels depicted in FIG. 5A can each provide flow perfusion in a direction orthogonal to the pneumatic microchannels, thereby allowing each individual microwell of the array to be independently addressable, through a specific combination of vacuum and perfusion, for relaxation and cell collection. Each perfusion channel and each pneumatic channel can be individually controlled.

The present technology provides a method for fabricating a reversible microwell device for capturing and analyzing cells, and further provides a method for cell isolation. The devices of the present technology can be provided as a kit of parts with instructions.

After isolation of single cells or groups of cells with a desired phenotype, the cells can be transferred, by microfluidic pathways or other means, to a lab-on-a-chip device, further cultivation devices, or further screening devices for sequencing, further analyses, culturing, or proliferation. For example, the advantages of the technology can eliminate or reduce the need for micropipetting, micromanipulation techniques, operationally complex processes, and cell sorting, which are expensive, time-consuming, low-throughput, and difficult to automate. The technology can be implemented in entirely automated systems eliminating the need for human intervention to isolate cells of interest.

EXAMPLES

Example 1: Isolation of Human Cells

Breast cancer cells can be cultured in about 5% $CO_2$ in air at about 37° C. in Roswell Park Memorial Institute 1640 medium supplemented with about 10% fetal bovine serum and trace of penicillin/streptomycin. The cells can be mildly trypsinized to further obtain a suspension of individual cells. A vacuum of about 500 mm Hg can be applied to the microwell device depicted in FIG. 4. Initially, vacuum is applied to the pneumatic channels such that all microwells are formed by drawing the elastomeric membrane fully down to conform with the microwell molds, for cell trapping. A suspension of the breast cancer cells is applied to the microwells of the array at a density of about $1\times10^6$ cells/mL, allowing single cells to settle into the microwells. The quality and distribution of the single cell loading of the array is viewed with an inverted microscope. After application of a chemotherapy agent, cells are imaged and analyzed. Surviving cells which are presumed resistant to DNA damage by the chemotherapy agent can be isolated by releasing the vacuum to microwells containing those cells and applying perfusion to collect the single cells in a collection reservoir. The resistant cells are then cultivated for another study using a different chemotherapy agent.

The invention claimed is:
1. A method for analysis and isolation of a plurality of single cells, the method comprising:
 (a) providing a single cell analysis and isolation system comprising
  a microfluidic device comprising
   a microwell substrate comprising a plurality of microwell molds, each microwell mold having an opening at an upper surface of the substrate, and one or more pneumatic microchannels connecting the microwells to an inlet for attaching a controllable vacuum source; and
   an elastomeric membrane bonded to the upper surface of the substrate and covering said microwell mold openings;
   wherein the elastomeric membrane is capable of conforming to each microwell mold when vacuum from said controllable vacuum source is applied through a said pneumatic microchannel connected to said microwell mold, thereby forming a microwell, and is capable of relaxing to form a planar surface above each microwell mold when pressure in the pneumatic microchannel connected to said microwell mold is returned to atmospheric pressure,
  a controllable vacuum source connectable to the pneumatic microchannels and operative to deform the elastomeric membrane of the microfluidic device,
  a microscope configured for observing cells in said microwells, and
  a controller for programmed operation of the controllable vacuum source and/or to direct vacuum to one or more selected pneumatic channels;
 (b) applying vacuum to one or more microwell molds of the device, whereby the elastomeric membrane forms microwells in said microwell molds;

(c) depositing a cell suspension onto the membrane of the device, whereby one or more cells of the cell suspension become entrapped within one or more of the microwells;

(d) analyzing one or more cells entrapped within the microwells using the microscope, whereby a characteristic of the one or more cells is determined; and (e) isolating cells having a characteristic of interest.

2. The method of claim 1, wherein the characteristic of the one or more cells is selected from the group consisting of an ability to produce antibodies or another cell secretion product, a secreted amount of antibodies or another cell secretion product, an immune cell-tumor cell interaction, expression of a gene, a cell phenotype, and a cell genotype.

3. The method of claim 1, wherein the isolating includes reducing vacuum applied to one or more microwell molds of the device.

4. The method of claim 1, further comprising:
(c1) allowing one or more cells to bind to a cell binding moiety disposed on an inner surface of one or more of the microwells.

5. The method of claim 1, wherein the analyzing includes use of said microscope, an imaging device, and imaging processing software.

6. The method of claim 1, wherein a single cell is deposited into one or more of the microwells.

7. The method of claim 1, further comprising:
(f) removal of one or more cells from the device for further analysis, cultivation, expansion, or use in a therapeutic method.

8. The method of claim 1, wherein the method includes reducing vacuum to one or more microwell molds of the device, whereby the elastomeric membrane relaxes above said microwell molds, the method further comprises perfusing a liquid over the relaxed membrane, thereby washing one or more cells from the membrane.

9. The method of claim 8, wherein the one or more cells washed from the membrane are collected in a cell pooling chamber of the device.

10. The method of claim 1, wherein the analyzing includes performing genomic analysis, performing proteomic analysis, or a combination thereof.

* * * * *